United States Patent [19]
Incavo et al.

[11] Patent Number: 5,830,215
[45] Date of Patent: Nov. 3, 1998

[54] REMOVAL APPARATUS AND METHOD

[76] Inventors: Stephen J. Incavo, 55 Butler Dr.; John F. Dirmaier, 27 Deerfield Rd., both of South Burlington, Vt. 05403

[21] Appl. No.: 870,771

[22] Filed: Jun. 6, 1997

[51] Int. Cl.$^6$ .................................................. A61B 17/56
[52] U.S. Cl. ................................................ 606/79; 606/99
[58] Field of Search ................................ 606/79, 83, 84, 606/86, 91, 99, 100; 128/749, 750, 751, 752, 753, 754

[56] References Cited

U.S. PATENT DOCUMENTS

| | | |
|---|---|---|
| 2,839,051 | 6/1958 | Chester . |
| 3,147,749 | 9/1964 | Marsh . |
| 3,357,422 | 12/1967 | Creelman . |
| 3,628,522 | 12/1971 | Kato . |
| 3,702,611 | 11/1972 | Fishbein . |
| 3,943,916 | 3/1976 | Vadas . |
| 4,271,849 | 6/1981 | Rehder . |
| 4,427,014 | 1/1984 | Bel et al. . |
| 4,611,587 | 9/1986 | Powlan . |
| 4,712,951 | 12/1987 | Brown . |
| 4,802,468 | 2/1989 | Powlan . |
| 4,817,630 | 4/1989 | Schintgen . |
| 4,896,663 | 1/1990 | Vandewalls . |
| 5,112,338 | 5/1992 | Anspach, III . |
| 5,228,451 | 7/1993 | Bales et al. . |
| 5,282,804 | 2/1994 | Salyer . |
| 5,405,404 | 4/1995 | Gardner et al. ............................ 623/23 |
| 5,417,693 | 5/1995 | Sowden et al. ............................ 606/85 |
| 5,486,181 | 1/1996 | Cohen et al. .............................. 606/91 |
| 5,507,296 | 4/1996 | Bales et al. . |
| 5,540,697 | 7/1996 | Rehmann et al. ......................... 606/91 |
| 5,562,102 | 10/1996 | Taylor . |
| 5,571,111 | 11/1996 | Aboczky ................................... 606/91 |

Primary Examiner—Guy V. Tucker
Attorney, Agent, or Firm—Domingue, Delaune & Waddell

[57] ABSTRACT

An apparatus and method for removing a previously implanted component is disclosed. Generally, the novel device will be used in artificial hip revision surgery. The device comprises a stem, a handle member adapted on the first end of the stem, and a hemispherical cutting blade mounted on the second end of the stem. The hemispherical cutting blade is adapted for cutting an acetabular component from the patient. In the preferred embodiment, the hemispherical cutting blade comprises a first-half hemispherical blade and a second-half hemispherical blade. The blades are interchangeable so that different size acetabular components may be removed via the procedure herein described. The device also includes a contact point member configured on the second end of the stem member, with the contact point member adapted to contact the concave surface of the acetabular component. The apparatus may further include an advancing member, operatively associated with the stem, for advancing the first-half hemispherical blade and said second-half hemispherical blade about said acetabular component. In one embodiment, the advancing member comprises a collar slidably received about the stem. The collar is movable relative to the stem so that as the collar is advanced, the hemispherical blades pivot about the acetabular component. A method of removing an acetabular component in a total hip replacement revision surgery with the hand tool is also disclosed.

8 Claims, 3 Drawing Sheets

REMOVAL APPARATUS AND METHOD

BACKGROUND OF THE INVENTION

This invention relates to an apparatus and method for removing surgical components from patients. More particularly, but not by way of limitation, this invention relates to an apparatus and method for removing an acetabular component from a patient.

Many people develop diseases of the hip that cause chronic discomfort and significant functional impairment. Total hip replacement (THR) is acknowledged as a highly successful procedure that has provided relief from pain, increased mobility, and improved tolerances for activity for thousands of people. Most patients have an excellent prognosis for long term improvement and symptoms in physical function. Primary total hip replacement is most commonly used for hip joint failure caused by osteoarthritis; other indications include, but are not limited to, rheumatoid arthritis, avascular necrosis, traumatic arthritis, certain hip fractures, benign and malignant bone tumors, arthritis associated with Paget's disease, ankylosing spondylitis, and juvenile rheumatoid arthritis. Recent changes have been made in fixation (cement and cement less) device designs, and some materials. Concerns remain about the in vivo durability of femoral and acetabular components of the implants.

Another important change in fixation has been the introduction and widespread use of non-cemented components that rely on bone growth into porous or onto roughened surfaces for fixation. In the femur, selected cementless components have exhibited clinical success, although with shorter follow-up, similar to that of cemented components installed with the newer cementing techniques. There is evidence that bone changes (osteolysis or bone resorption) can occur as well with some of the cementless components. On the acetabular side, the cementless components have demonstrated less aseptic loosening as compared with the cemented components over the short term, long term results are not yet available. Synthetic bio-materials currently used in THR include alloys such as cobalt-chromium, and titanium based systems, and polymers such as polyethylene.

Despite these advances, however, certain deficiencies remain. The THR may fail for several reasons, including mechanical reasons or for reasons associated with infection. Revision of the total hip replacement is indicated when mechanical failure occurs. The revision surgery is technically more difficult and the long term prognosis is generally not as good as for primary THR. The optimal surgical techniques for THR revision vary considerably depending on the conditions encountered.

Recent studies have shown that to a very high degree bone successfully grows into porous surfaces of the acetabular component. Thus, in a revision surgery, it is exceedingly difficult to remove the acetabular component, and the surgeon has no good option available. The prior art teaches use of various hand tools that have been designed to remove the acetabular component. For instance, in U.S. Pat. No. 5,112,338 to Anspach, the disclosure teaches a surgical instrument for removing artificial acetabular cups. The instrument utilizes a hand held surgical rotary impact tool and instrument extension for removing the acetabular cup of a hip joint. However,)tools such as these have proven to be inadequate.

Therefore, there is a need for a hand apparatus that can be used by a surgeon in order to precisely remove previously implanted components. There is also a need for apparatus and method that can be used in order to remove an acetabular component in total hip replacement revision surgery. Further, there is a need for a device and method that removes bone growth into an acetabular component.

SUMMARY OF THE INVENTION

An apparatus and method for removing previously implanted components is disclosed. Generally, the novel device will be used in THR revision surgery. Generally, the device comprises a stem, a handle member adapted on the first end of the stem, and a hemispherical cutting blade mounted on the second end of the stem. The hemispherical cutting blade is adapted for cutting an acetabular component from the patient.

In the preferred embodiment, the hemispherical cutting blade comprises a first-half hemispherical blade and a second-half hemispherical blade. The blades are interchangeable so that different size acetabular components (diameters) may be removed via the procedure herein described. The device also includes a contact point member configured on the second end of the stem member, with the contact point member adapted to contact the concave surface of the acetabular component or to engage the central hole, if present, or the acetabular component.

The apparatus may further include a first blade holder adapted to receive the first-half hemispherical blade, and a second blade holder adapted to receive the second-half hemispherical blade. Also included may be an advancing means, operatively associated with the stem, for advancing the first-half hemispherical blade and said second-half hemispherical blade about said acetabular component. In one embodiment, the advancing means comprises a collar slidably received about the stem. The collar is movable relative to the stem so that as the collar is advanced, the hemispherical blades pivot about the acetabular component.

Also disclosed is a method of removing an acetabular component in a total hip replacement revision surgery. The method is preformed with the novel hand tool. The method comprises preparing the patient for acetabular component removal which includes exposing the acetabular component for the procedure. Next, the surgeon identifies the circumference of the acetabular component and places the tool into the concave area of the acetabular component which may include centering the tip into the concave acetabular surface or locking into the central hole. The surgeon will position the first half hemispherical blade and the second half hemispherical blade onto the edge of the acetabular shell and rotate the hand tool so that the first half hemispherical blade and the second half hemispherical blades are turned about the horizontal axes. The rotation about the horizontal axes cuts an amount of bone at the component rim. In the preferred embodiment, it is necessary to cut only a small amount.

Thereafter, the surgeon may begin to advance the blades incrementally downward. This is performed by rotating a collar configured about the stem so that the collar is advanced against the first hemispherical blade and the second hemispherical blade. Simultaneously therewith, the surgeon may rotate the tool about the horizontal axes which also aids the blades in cutting. Once the blades have been properly extended, the surgeon may terminate the downward advancement. If the surgeon was also rotating the hand tool about the horizontal axes, that rotation may also be terminated. Once the first hemispherical blade and the second hemispherical blade have been properly advanced, no fixation impediment will exist for the shell removal.

In one embodiment, the hand tool further comprises a contact point extending from the second end of the stem, and wherein the step of placing the hand tool about the acetabular component includes locating the contact point on the concave surface of the acetabular component.

An advantage of the present device is that it may be used in total hip replacement revision surgery. Another advantage is that the device may be used for removal of cementless acetabular components. Yet another advantage is that the device and method is designed to cut the bone-metal interface in a slowly advancing fashion. Still yet another advantage is that the device and method may be used with varying size acetabular cup components.

A feature of the present invention includes employment of a hemispherical blade. Another feature is that the hemispherical blade may be divided in two halves. Yet another feature is that the hemispherical blades are interchangeable in order to conform with different size surgical components to be removed.

Another feature includes the pivoting of the blades is initiated by collar movement interacting with the blade holders to force the blades to pivotly advance about the component. Yet another feature is the knurled collar that is disposed about the stem which allows for the incremental advancement of the blades about the component. Still yet another feature is a contact point member placed within the concave surface of the component that allows for a foundation for the application of a downward force. Yet another feature is that the teachings of the present invention may be applied to the removal of other components. Another feature includes locking the device into the central hole of the component.

DETAILED DESCRIPTION OF THE PREFERRED EMBODIMENTS

Figure 1B:
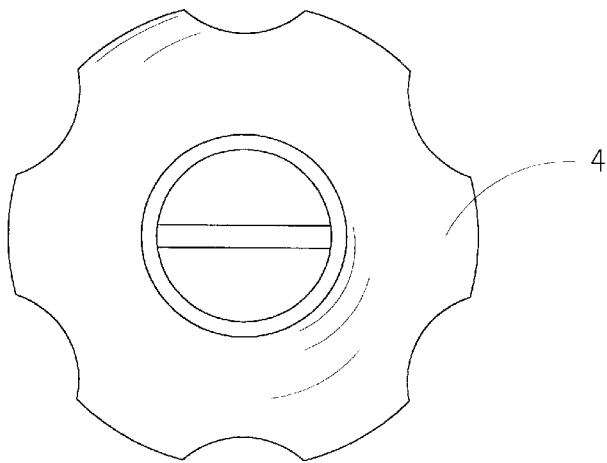
FIG. 1B is a top plan view of the removal apparatus of FIG. 1A.
Figure 1A:
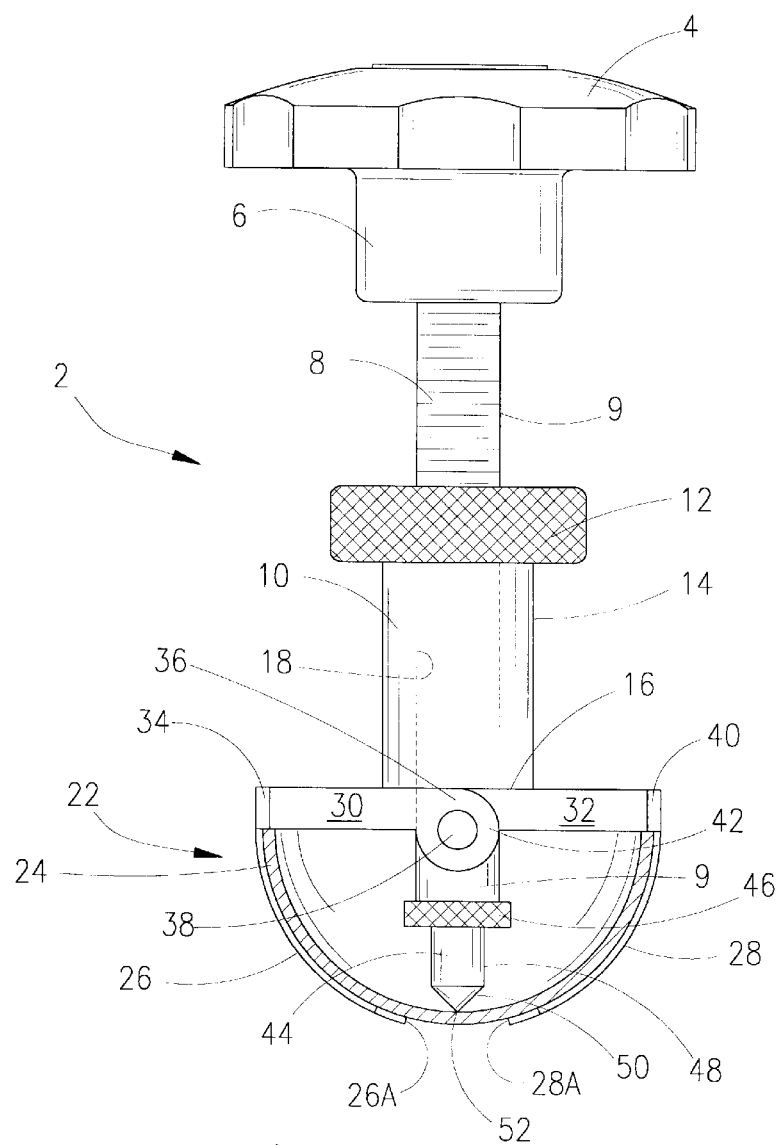
FIG. 1A is a front plan view of the removal apparatus of the present invention.

Referring to FIG. 1A, a front plan view of the removal apparatus 2 of the present invention will now be described. Generally, the apparatus 2 will contain a palm ratchet handle 4 that is adapted to be easily received within the hands of the surgeon. The palm ratchet handle 4 extends to a cylindrical member 6, with the cylindrical member 6 having an internal bore.

The internal bore of the cylindrical member 6 will receive the stem 8. The stem 8 will have an outer surface 9 that will have formed thereon external thread means which will allow the advancement of the blades according to the teachings of the present invention, all of which will be described later in the application. Alternatively, the stem 8 could contain a series of serrations that would be used as a ratchet-pawl device. The stem 8 will be operatively associated with the collar member 10. In the preferred embodiment, the collar member 10 comprises an outer knurled first outer surface 12 that extends to the second outer surface 14 which in turn terminates at the end radial surface 16.

The collar member 10 also contains an inner diameter 18, with the inner diameter 18 having cooperating thread means for engagement with the thread means formed on the stem 8. Thus, the surgeon may advance the collar member 10 relative to the stem 8 in small lateral increments via rotation of the handle 4. Alternatively, the inner diameter 18 may have projections and grooves that would cooperate with the serrations formed on the stem 8 thereby forming a ratchet mechanism for the advancement of the blades 26, 28.

The cutting means, seen generally at 22, for cutting the acetabular component from the patient will now be described. Generally, the cutting means 22 will include a hemispherical blade member, with the hemispherical blade member being of a size and circumference that corresponds with the contour of the acetabular component 24. In the preferred embodiment, the hemispherical blade member contains a first-half 26 of said hemispherical blade, and a second-half 28 of said hemispherical blade. The blades 26, 28 are operatively associated with the second end of the stem 8. The blade 26 concludes at the cutting edge 26A, while the blade 28 concludes at the cutting edge 28A. Thus, as seen in FIG. 1A, the blades 26, 28 have been advanced a considerable extent about the acetabular component 24.

The apparatus 2 will further contain the blade holders 30,32. The blade holder 30 will have an outer end 34 that is attached to the first-half hemispherical blade 26. The outer end 34 extends to the inner end 36, with the end 36 having an opening. The opening contains a center axial shaft 38 about which the blade holders 30, 32 will pivot as will be more fully explained later in the application. The blade holder 32 will also have an outer end 40 that is attached to the second-half hemispherical blade 28. The outer circumference 40 concludes at the inner end 42, with the end 42 having an opening that will also have the center axial shaft 38 contained therein.

The apparatus 2 also has associated therewith the contact point member 44, with the point member 44 being attached to the stem 8. The point member 44 may be joined to the stem 8 by conventional means, such as thread means. The point member 44 contains a first outer surface 46 that extends to the second outer surface 48 which in turn stretches to the conical surface 50 and concludes at the apex 52. The apex 52 may be placed within a central hole of the component 24. As seen in FIG. 1B, a top plan view of the removal apparatus 2 of FIG. 1A will now be described. As shown, the ratchet handle 4 is made with indentations for gripping by the surgeon.

Figure 2B:
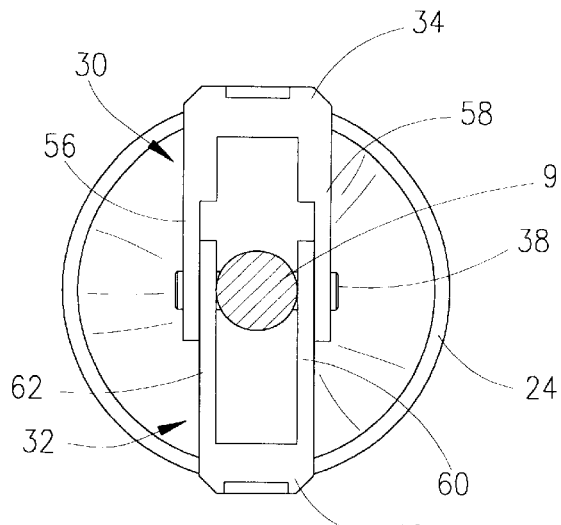
FIG. 2B is a top plan sectional view of the removal apparatus of FIG. 2A.
Figure 2A:
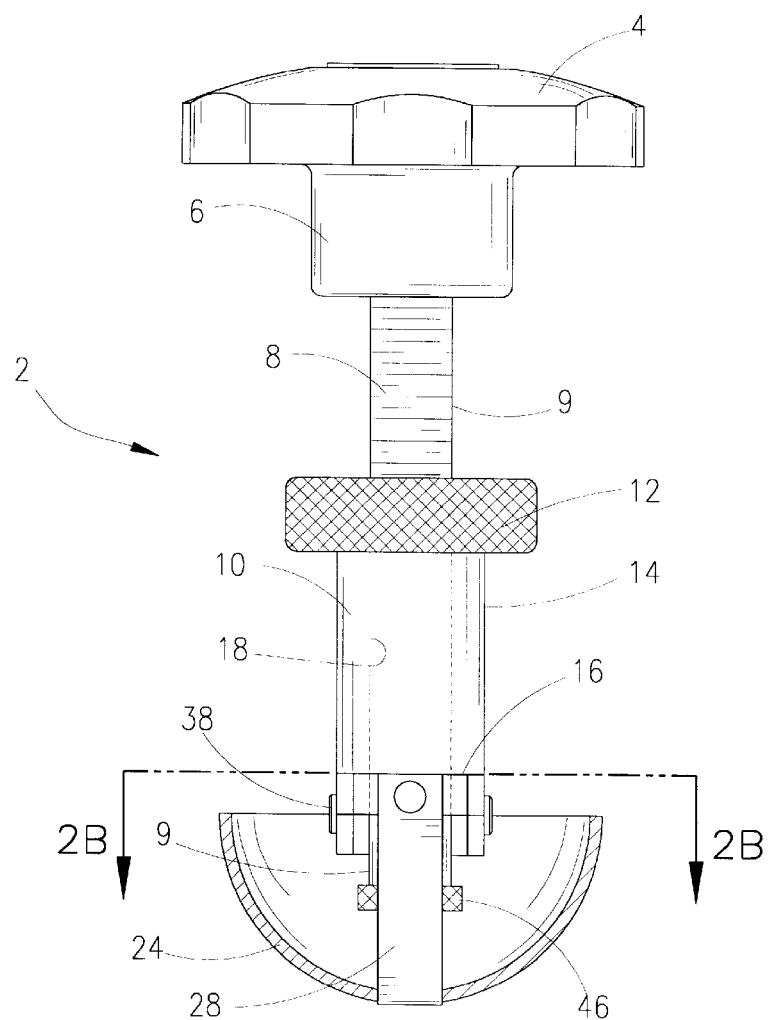
FIG. 2A is a side plan view of the removal apparatus of FIG. 1A.

In FIG. 2A, the side plan view of the novel removal apparatus 2 of FIG. 1A will now be described. It should be noted that like numbers appearing in the various figures refer to like components. Thus, in this view, the cooperation of the blade holders 30, 32 about the center axial shaft 38 is better depicted. In FIG. 2B, a top plan sectional view of the removal apparatus 2 of FIG. 2A illustrates the opposing blade holders 30,32. The blade holder 30 will have two arms 56,58 that extend from the end 34. The arms 56, 58 have the opening formed therethrough so that the center axial shaft 38 is placed therethrough. The blade holder 32 will also have two arms 60,62 that extend from the end 40. The arms 60, 62 have the opening formed therethrough so that the center axial shaft 38 is placed therein. The ends 32, 34 will have attached thereto the blades 26, 28 respectively, in a conventional manner such as by clamping.

Figure 3:
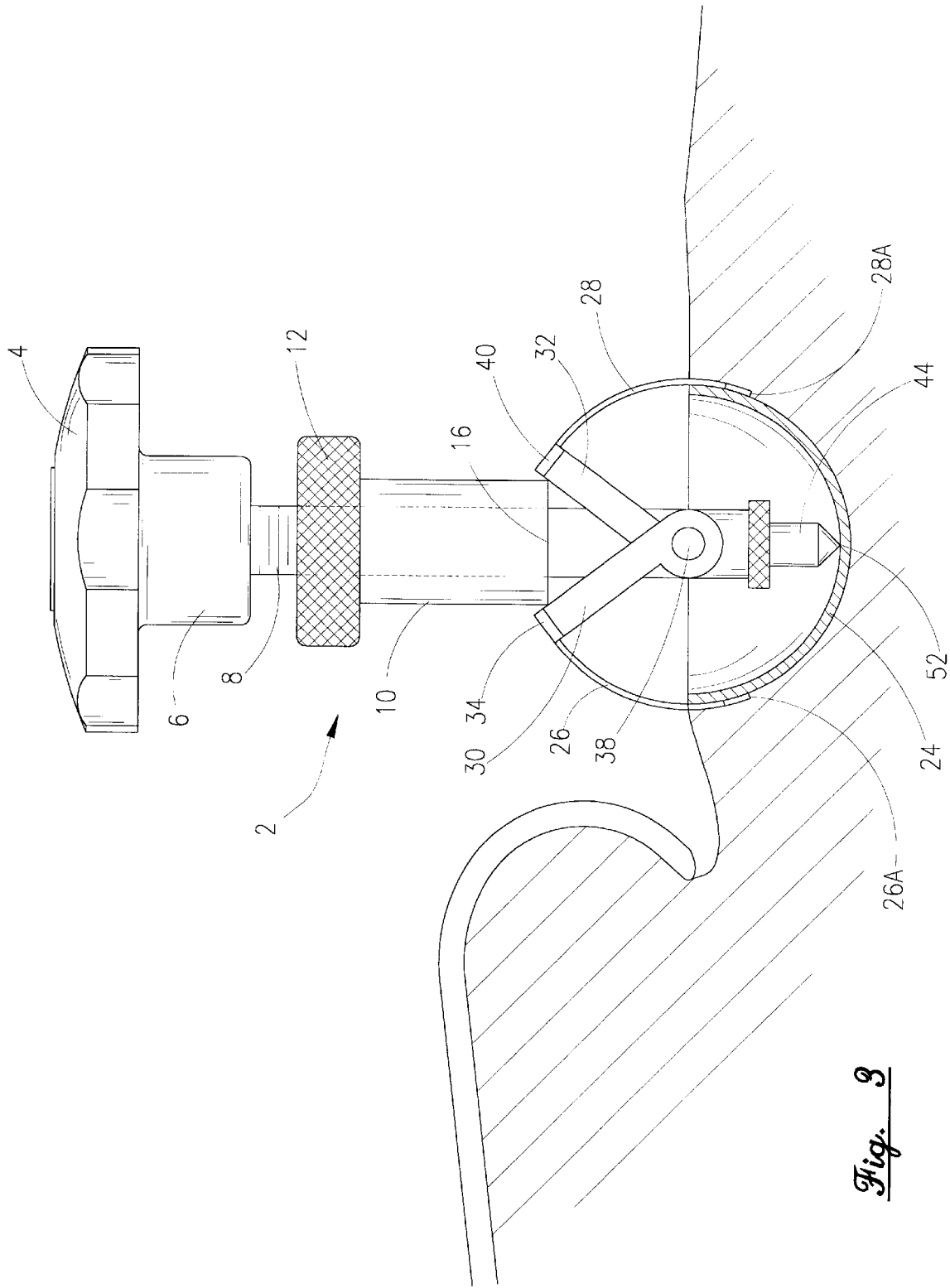
FIG. 3 is an illustrated view showing the removal tool of the present invention being advanced about a component to be removed.

OPERATION:

The operation of the present invention will now be described with reference to FIG. 3, which illustrates the removal apparatus 2 being positioned for advancement about the acetabular cup component 24. The component 24 was previously implanted to the pelvis region of a patient who had undergone a total hip replacement for instance, as is well understood by those of ordinary skill in the art. The procedure of the present invention would include having the surgeon place the contact point member 44 within the concave center portion of the acetabular component 24. The acetabular component 24 may contain a center hole therein so that the apex 52 of the contact point member 44 may be placed therein. The blades 26, 28 are chosen so that the circumference conforms to the circumference of the acetabular component 24.

The surgeon will prepare the patient for the surgery which includes exposing the acetabular component 24 which in turn allows the surgeon to identify the acetabular rim. The surgeon may use standard tools such as curettes, osteotomes and periosteal elevators to expose the rim. In the case where the acetabular component contains a polyethylene liner, the liner should be removed to expose the articular side of the acetabular shell. Also, if there are any acetabular fixation screws, those screws should also be removed. The appropriate sized cutting blades will be chosen.

The method will include placing the hand tool 2 into the central acetabular hole and locking the tool into place by placing the apex 52 into the central hole. It should be noted that the central hole may have internal threads so that the contact member may be threadedly locked into position by placing mating threads onto the apex 52. If no central acetabular hole exist, the surgeon will place the tool into the center of the dome so that the contact point 44 comes into contact with the concave surface. The appropriate sized cutting blades 26, 28, previously assembled, are then placed onto the edge of the acetabular shell by turning the blades 26, 28 in a circular fashion about the horizontal axes. The cutting blades 26, 28 should cut through a small amount of bone at the rim. Once this amount has been cut circumferentially, the blades are advanced a small amount and the circular cutting motion is repeated.

The surgeon may then begin rotating the collar member 10 by means of the cooperating threads on the stem 8 and the inner diameter of the collar 10 which in turn will have the radial surface 16 act against the ends 32 and 34 of the blade holders. The blades 26, 28 may be advanced slowly. The rotation of the palm handle 4 in conjunction with the thread means will enable the collar to proceed in only the downward direction. The operator will continue to advance the blades 26, 28 by rotation of the handle 4 and the downward force of the collar member 10. Due to the hemispherical shape of the blades 26, 28, the blades will advance by the pivoting about the center of the cup 24 cutting a hemispherical bore. The pivoting of the blades 26, 28 takes place about the center axial shaft 38. The blades will effectively cut the bone ingrowth into the acetabular component 24.

The surgeon will continue this procedure until the blades have cut a hemisphere to the level of the dome of the acetabular shell. Once this is completed, there will no longer be a fixation impediment and the component may be removed. It should be noted that the apparatus 2 may also be used for removal of other types of components such as those components that have a cement interface. Also, the apparatus may be used to remove other types of components implanted within a patient.

Changes and modifications in the specifically described embodiments can be carried out without departing from the scope of the invention which is intended to be limited only by the scope of the appended claims.

We claim:

1. An apparatus for removing an acetabular component previously implanted to a patient comprising:

a stem member having a first end and a second end, and wherein said stem member contains thread means;

a handle member adapted on said first end of said stem member;

cutting means, mounted on said second end of said stem, for cutting the acetabular component from the patient, and wherein said cutting means comprises a hemispherical blade including a first blade comprising a first-half of said hemispherical blade and a second blade comprising a second-half of said hemispherical blade; and, a collar having a first end and a second end, wherein said collar is slidably received about said stem; and wherein said collar engages said thread means so that rotation of said collar advances said collar downward relative to said stem and wherein said first end of said collar is engaged with said first blade and said second blade.

2. The apparatus of claim 1 wherein the acetabular component contains a concave surface, and the apparatus further comprises:

a contact point member configured on said second end of said stem member, said contact point member adapted to contact the concave surface of the acetabular component.

3. The apparatus of claim 1 further comprising:

a first blade holder adapted to receive said first half of said hemispherical blade;

a second blade holder adapted to receive said second half of said hemispherical blade.

4. A device used in artificial hip revision surgery comprising:

a stem member having a first end and a second end;

a handle member adapted on said first end of said stem member;

a hemispherical cutting blade, mounted on said second end of said stem, adapted for cutting an acetabular component from the patient, and wherein said hemispherical cutting blade comprises a first-half hemispherical blade and a second-half hemispherical blade;

a contact point member configured on said second end of said stem member, said contact point member adapted to contact the concave surface of the acetabular component;

a first blade holder adapted to receive said first-half hemispherical blade;

a second blade holder adapted to receive said second-half hemispherical blade; and advancing means, operatively associated with said stem, for advancing said first-half hemispherical blade and said second-half hemispherical blade about said acetabular component, wherein said advancing means comprises a collar having a first end and a second end, said collar being slidably received about said stem, said collar engaging said thread means so that said collar is advanced, and wherein said first end of said collar is engaged with said first blade holder and said second blade holder.

5. The apparatus of claim 4 wherein said first-half hemispherical blade is interchangeable.

6. A method of removing an acetabular component in a total hip replacement revision surgery with a hand tool, said hand tool comprising: a stem member having a first end and a second end; a handle member adapted on said first end of said stem member; and, a first-half hemispherical cutting blade and a second-half hemispherical cutting blade, said first-half and said second half hemispherical cutting blade being configured on said second end of said stem, said method comprising:

preparing the patient for acetabular component removal;

exposing the acetabular component;

identifying the circumference of the acetabular component;

placing the tool into the concave area of the acetabular component;

placing the first half hemispherical blade and the second half hemispherical blade onto the edge of the acetabular shell;

rotating the hand tool so that the first half hemispherical blade and the second half hemispherical blades are turned about the horizontal axes;

cutting an amount of bone at the rim by said rotation;

advancing the blades incrementally downward about the stem while also continuing to rotate the tool about the horizontal axes;

terminating the advancement of the blades;

terminating the rotation of the hand tool about the horizontal axes;

removing the acetabular component.

7. The method of claim 6 wherein said hand tool further comprises a contact point extending from the second end of said stem, and wherein said step of placing said hand tool about the acetabular component includes:

locating the contact point on the concave surface of the acetabular component.

8. The method of claim 7 wherein said hand tool further comprises a collar having a first end and a second end, said collar being slidably received about said stem, said collar engaging said thread means so that said collar is incrementally advanced, and wherein said collar is operatively associated with said first-half hemispherical and said second-half hemispherical blade;

and, wherein the step of advancing said first-half hemispherical and said second-half hemispherical cutting blade about the stem comprises downwardly rotating on said collar so that the collar forces said first-half hemispherical blade and said second-half hemispherical blade downward about the acetabular component.

* * * * *